United States Patent [19]
Ehrenberg et al.

[11] Patent Number: 5,998,380
[45] Date of Patent: Dec. 7, 1999

[54] TREATMENT OF MIGRAINE

[75] Inventors: Bruce L. Ehrenberg, Boston; Anita K. Wagner, Arlington, both of Mass.

[73] Assignee: New England Medical Center Hospitals, Inc., Boston, Mass.

[21] Appl. No.: 08/542,950

[22] Filed: Oct. 13, 1995

[51] Int. Cl.[6] .................................................. A61K 31/70
[52] U.S. Cl. ............................ 514/23; 514/459; 514/517
[58] Field of Search ................................ 514/23, 459, 517

[56] References Cited

U.S. PATENT DOCUMENTS

| | | | |
|---|---|---|---|
| 2,554,816 | 5/1951 | Clapp et al. | 260/290 |
| 2,980,679 | 4/1961 | Pala | 260/256.5 |
| 4,513,006 | 4/1985 | Maryanoff et al. | 514/23 |
| 4,792,569 | 12/1988 | Maryanoff et al. | 514/517 |
| 5,242,942 | 9/1993 | Costanzo et al. | 514/439 |
| 5,258,402 | 11/1993 | Maryanoff | 514/454 |
| 5,384,327 | 1/1995 | Costanzo et al. | 514/456 |

OTHER PUBLICATIONS

Harrison's Principles of Internal Medicine, eds. Isselbacher et al., McGraw–Hill, Inc., New York, 1994, vol. 1, Chapter 14, pp. 65–71.

*Primary Examiner*—Elli Peselev
*Attorney, Agent, or Firm*—Fish & Richardson P.C.

[57] ABSTRACT

A method for treating migraine in non-epileptic subjects which involves administering to subjects an effective amount of a pharmaceutical composition comprising a sulfamate of the following formula:

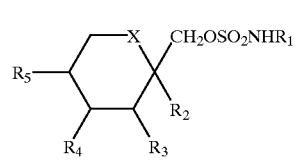

14 Claims, No Drawings

TREATMENT OF MIGRAINE

BACKGROUND OF THE INVENTION

This invention relates to treatment of migraine syndrome.

Description of Related Art

A working definition of migraine is a benign recurring headache and/or neurologic dysfunction, more common in women than men.

Classic migraine (migraine with aura) refers to the syndrome of a severe, throbbing headache which often is preceded by sensory, motor or visual symptoms, referred to as an "aura." Common migraine (migraine without aura) denotes a headache without the aura. Common migraine is the most frequent headache type reported by patients.

Many drugs are now available for prophylactic treatment of migraine. They must be taken daily. The major drugs for prophylaxis are propranolol, amitriptyline, valproate, verapamil, phenelzine, and methysergide. Use of methysergide carries with it the danger of retroperitoneal fibrosis. Aspirin-like drugs, including aspirin, naproxen, ibuprofen, mefenamic acid, flufenamic acid, and tolfenamic acid are in use as prophylactic agents. The high dosage of these compounds required for effectiveness is a drawback. It has been estimated that the probability of success with any one of the available prophylactic antimigraine drugs is about 60 to 75% (Harrison's Principles of Internal Medicine, eds. Isselbacher et al., McGraw-Hill, Inc., New York, 1994, p. 69). Accordingly, development or identification of drugs for prophylactic treatment of migraine is an area of continuing medical need.

SUMMARY OF THE INVENTION

The invention features administering sulfamates of the following formula (I):

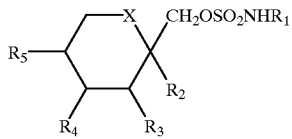

wherein X is O or $CH_2$ and $R_1$, $R_2$, $R_3$, $R_4$, and $R_5$ are as hereinafter defined, to prophylactically control migraines in non-epileptic subjects. The most preferred compound is topiramate, described below. Topiramate has been used to treat epileptics, including epileptics who suffer from migraine, to prevent seizures.

The above discussed and other features and attendant advantages of the present invention will become better understood by reference to the following detailed description of the invention, and from the claims.

DETAILED DESCRIPTION

By treating migraine patients with the sulfamate compound of formula (I) or a pharmaceutically acceptable salt or derivative thereof, a substantial decrease in frequency of migrainous episodes can be achieved.

The administered compound is a sulfamate of the following formula:

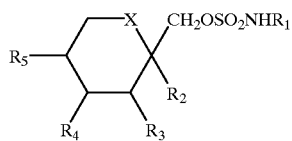

wherein
X is $CH_2$ or oxygen;
$R_1$ is hydrogen or lower ($C_1$–$C_6$) alkyl; and
$R_2$, $R_3$, $R_4$ and $R_5$ are independently hydrogen or lower alkyl and, when X is $CH_2$, $R_4$ and $R_5$ may be alkene groups joined to form a benzene ring and, when X is oxygen, $R_2$ and R3 and/or $R_4$ and $R_5$ together may be a methylenedioxy group of the following formula (II):

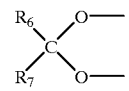

wherein
$R_6$ and $R_7$ are the same or different and are hydrogen, lower alkyl or are alkyl and are joined to form a cyclopentyl or cyclohexyl ring,
$R_1$ in particular is hydrogen or alkyl of about 1 to 4 carbons, such as methyl, ethyl and iso-propyl. Alkyl throughout this specification includes straight and branched chain alkyl. Alkyl groups for $R_2$, $R_3$, $R_4$, $R_5$, $R_6$, and $R_7$ are preferably of about 1 to 3 carbons and include methyl, ethyl, iso-propyl and n-propyl. When X is $CH_2$, $R_4$ and $R_5$ may combine to form a benzene ring fused to the 6-membered X-containing ring, i.e., $R_4$ and $R_5$ are defined by the alkatrienyl group =CH—CH=CH—CH=.

In a particular group of compounds of formula (I), X is oxygen and both $R_2$ and $R_3$ and $R_4$ and $R_5$ together are methylenedioxy groups of the formula (II) wherein R6 and $R_7$ are both hydrogen, both alkyl or combine to form a spiro cyclopentyl or cyclohexyl ring, in particular where $R_6$ and $R_7$ are both alkyl such as methyl. A second group of compounds is that wherein X is $CH_2$ and $R_4$ and $R_5$ are joined to form a benzene ring. A third group of compounds of formula (I) is that wherein both $R_2$ and $R_3$ are hydrogen.

Compounds of formula I which are preferred for use in the method of the invention are tetrahydro-2H-pyran-2-yl) methane sulfamate, 2,3:4,5-bis—O—(1-methylethyldiene)-β-D-fructopyranose sulfamate, and 2,3:4,5-bis—O—(1-methylethyldiene)-β-D-fructopyranose methylsulfamate. A most preferred compound is 2,3:4,5-bis—O—(1-methylethyldiene)-β-D-fructopyranose sulfamate, also known as topiramate, having the chemical structure shown in formula III:

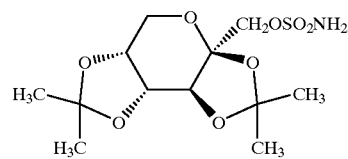

By pharmaceutically acceptable derivative is meant any pharmaceutically acceptable ester or salt of such ester of the compounds of formula (I) or any other compounds which upon administration to the recipient is capable of providing (directly or indirectly) a compound of formula (I) or an anti-migraine active metabolite or residue thereof.

It will be appreciated by those skilled in the art that the compounds of formula (I) may be modified to provide pharmaceutically acceptable derivatives thereof at any of the functional groups in the compounds. Of particular interest are derivatives in which the sulfamate portion is masked by an imidate group that can be removed in a physiological milieu to generate the parent drug, as disclosed in U.S. Pat. No. 5,258,402, and incorporated herein by reference. Such derivatives are commonly known as prodrugs. Other derivatives of interest include sorbopyranose sulfamates (U.S. Pat. No. 5,384,327), fructopyranose cyclic sulfites and sulfates (U.S. Pat. No. 5,242,942), and phenylethyl sulfamates (U.S. Pat. No. 4,792,569), as well as acetazolamide (U.S. Pat. Nos. 2,554,816 and 2,980,679).

It will be appreciated by those skilled in the art that the pharmaceutically acceptable derivatives of the compounds of formula (I) may be derivatised at more than one position.

Pharmaceutically acceptable salts of the compounds of formula (I) include those derived from pharmaceutically acceptable, inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulphonic, tartaric, acetic, citric, formic, benzoic, malonic, napthalene-2-sulphonic and benzenesulphonic acids. Other acids such as oxalic acid, while not in themselves pharmaceutically acceptable, may be useful in the preparation of salts useful as intermediates in obtaining compounds useful in the method of the invention and their pharmaceutically acceptable acid addition salts.

Salts derived from appropriate bases include alkali metal (e.g. sodium), alkaline earth metal (e.g. magnesium) ammonium and $NR_4$ (where R is $C_{1-4}$ alkyl) salts.

Synthesis. The anti-migraine sulfamate derivatives employed in the method of the invention can be synthesized according to the methods disclosed in U.S. Pat. No. 4,513,006, which is incorporated by reference. Other methods well known in the art for preparing the disclosed sulfamate compounds, precursors, prodrugs, or derivatives thereof are also available, for example, those disclosed in U.S. Pat. Nos. No. 5,258,402, 5,384,327, 5,242,942, 4,792,569, 2,554,816 and 2,980,679, all of which are incorporated by reference.

Pharmaceutical Compositions. Pharmaceutical compositions of the anti-migraine sulfamate derivatives of the invention can be prepared according to the methods disclosed in U.S. Pat. No. 4,513,006, which is incorporated by reference.

Treatment and Dosage. The amount of a compound of formula (I) useful for treatment of migraine in non-epileptic subjects will vary not only with the particular compound selected but also with the route of administration, and the age and condition of the patient treated. In general, suitable doses are in the range of from about ½ to 15 mg/kg body weight per day, preferably in the range of 1 to 10 mg/kg day, most preferably in the range of 1 to 5 mg/kg day. The method of the invention can conveniently administer daily dosages of compounds of formula (I) in unit dosages, for example, containing 50 to 400 mg, conveniently 100 to 200 mg, of active ingredient per unit dosage form. Suitable treatment is given 1 or 2 times daily, depending upon clearance rate. Accordingly, the desired dose may be presented in a single dose or as divided doses administered at appropriate intervals, for example as two, three, four or more sub-doses per day.

Treatment is preferably commenced before the onset of a migraine episode and continued indefinitely.

While it is possible that, for use in the method of the invention, compounds of formula (I) may be administered as the raw chemical, it is preferable to present the active ingredient as a pharmaceutical formulation or composition which may further include a pharmaceutically acceptable carrier. The carrier must be 'acceptable' in the sense of being compatible with the other ingredients of the formulation and not deleterious to patient.

The following examples are intended to illustrate but not limit the invention. While they are typical, other procedures known to those skilled in the art may alternatively be used to illustrate the embodiments and methods of the invention.

EXAMPLES

Example 1

ANTI-MIGRAINE ACTIVITY IN EPILEPTIC PATIENTS

The following example falls outside the scope of the appended claims.

Patient 1, an epileptic, suffered from complex partial seizures and frequent episodes of migraine, some of which were temporally related to his seizures. Seizures and migraines were incompletely responsive to large doses of calcium channel blockers added to his anti-epileptic drug regimen. Patient 2 suffered from complex partial seizures and frequent, severe migraine episodes, requiring regular use of sumatripan.

Patient 1 took topiramate daily for 18 months. Patient 2 took topiramate daily for 10 months.

Patient 1 used 600 mg/d with substantial improvement in migrainous episodes; his current dosage is 800 mg/d. Patient 2 used 400 mg/d with substantial improvement of her migraine headaches.

Except for one migrainous aura, Patient 1's migraine episodes were nearly completely controlled and all calcium channel blockers were able to be withdrawn. Patient 1 did not experience any adverse effects from topiramate. Patient 2 had several episodes of basilar migraine without headache in the fifth and sixth months of toipramate use during brief cessation of her propranolol therapy, but was migraine-free thereafter until the tenth month, when she experienced 2 nocturnal generalized tonic clonic seizures, and subsequently died.

After taking 800 mg/d of topiramate, Patient 1 had not experienced any migrainous episodes. Verapamil, nimodipine, and cimetidine (given to increase verapamil levels) were successfully withdrawn. Patient 2 experienced substantially less frequent migraine headaches after taking topiramate 200 mg/d, eliminating the average use of 2 administrations of sumatriptan per week once she was taking 300 mg/d of topiramate.

Example 2

ANTI-MIGRAINE ACTIVITY IN NON-EPILEPTIC PATIENTS

To prevent migraine in non-epileptic patients, an effective amount of a pharmaceutical composition containing a sulfamate of formula (I), in particular 2,3:4,5-bis—O—(1-methylethyldiene)-β-D-fructopyranose sulfamate (topiramate) is orally administered daily to the patient. The daily dosage is in the range of about 50 mg to 1000 mg for an average adult human.

What is claimed is:

1. A method of reducing the frequency or severity of migrainous episodes in a non-epileptic human patient, said method comprising administering to the patient an effective amount of a sulfamate of the following formula (I):

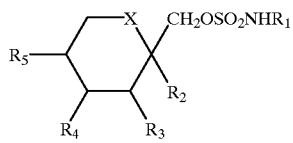

I wherein
X is oxygen;
R₁ is hydrogen or lower alkyl; and
R₂, R₃, R₄ and R₅ are independently hydrogen or lower alkyl and R₂ and R₃ and/or R₄ and R₅ together are a group of the following formula (II):

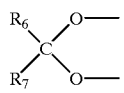

II wherein
R₆ and R₇ are the same or different and are hydrogen, lower alkyl or are alkyl and are joined to form a cyclopentyl or cyclohexyl ring.

2. The method of claim 1, wherein R₂ and R₃, and R₄ and R₅, together are groups of the formula (II).

3. The method of claim 1, wherein R₁ is alkyl of about 1 to 4 carbons; said lower alkyl group for R₂, R₃, R₄ and R₅ is alkyl of about 1 to 3 carbons; and said lower alkyl for R₆ and R₇ is alkyl of about 1 to 3 carbons.

4. The method of claim 1, wherein said sulfamate of formula (I) is selected from the group consisting of:
(tetrahydro-2H-pyran-2-yl)methane sulfamate;
2,3:4,5-bis—O—(1-methylethyldiene)-β-D-fructopyranose sulfamate; and
2,3:4,5-bis—O—(1-methylethyldiene)-β-D-fructopyranose methylsulfamate.

5. The method of claim 4, wherein said sulfamate is 2,3:4,5-bis—O—(1-methylethyldiene)-β-D-fructopyranose sulfamate.

6. The method of claim 4 wherein the sulfamate is 2,3:4,5-bis—O—(1-methylethyldiene)-β-D-fructopyranose methylsulfamate.

7. The method of claim 1, wherein said sulfamate is administered with a pharmaceutically acceptable carrier.

8. The method of claim 1, wherein said sulfamate is present in a unit dosage amount of about 50 to 400 milligrams.

9. The method of claim 1, wherein the two oxygen atoms of the group of formula (II) are attached on the same side of the six-membered ring depicted in formula (I).

10. The method of claim 1, wherein the sulfamate of formula (I) is a sulfamate of fructopyranose.

11. The method of claim 1, wherein in formula (I), R₁ is hydrogen.

12. A method of treating migraine in a non-epileptic human patient, said method comprising administering to the patient an effective amount of a sulfamate of the following formula (I):

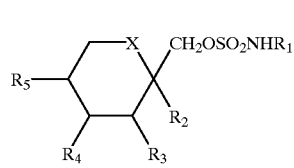

(I)

wherein
X is CH₂;
R₁ is hydrogen or lower alkyl; and
R₂, R₃, R₄, and R₅ are independently hydrogen or lower alkyl and R₂ and R₃ and/or R₄ and R₅ together are a group of the following formula (II)

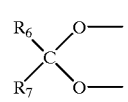

(II)

wherein
R₆ and R₇ are the same or different and are hydrogen, lower alkyl or are alkyl and are joined to form a cyclopentyl or cyclohexyl ring.

13. A method of reducing the frequency or severity of migrainous episodes in a non-epileptic patient, the method comprising administering to the patient a compound consisting of the sulfamate of claim 1 and an imidate group that
(a) masks the sulfamate portion of the sulfamate of claim 1, and
(b) can be removed in a physiological milieu to generate the sulfamate of claim 1.

14. A method of reducing the frequency or severity of migrainous episodes in a non-epileptic patient, the method comprising administering to the patient a sorbopyranose sulfamate, a fructopyranose cyclic sulfite, a fructopyranose cyclic sulfate, a phenylethyl sulfamate, acetazolamide, or methazolamide.

* * * * *